(12) United States Patent
Huguet Clotet et al.

(10) Patent No.: US 7,741,492 B2
(45) Date of Patent: Jun. 22, 2010

(54) METHOD FOR OBTAINING A PHARMACEUTICALLY ACTIVE COMPOUND (IRBESARTAN) AND ITS SYNTHESIS INTERMEDIATE

(75) Inventors: Joan Huguet Clotet, Sant Joan Despi (ES); Pere Dalmases Barjoan, San Feliu De Llobregat (ES)

(73) Assignee: Inke, S.A., Castellbisal (ES)

( * ) Notice: Subject to any disclaimer, the term of this patent is extended or adjusted under 35 U.S.C. 154(b) by 0 days.

(21) Appl. No.: 11/909,757

(22) PCT Filed: Feb. 23, 2006

(86) PCT No.: PCT/EP2006/060208

§ 371 (c)(1),
(2), (4) Date: Sep. 26, 2007

(87) PCT Pub. No.: WO2006/089927

PCT Pub. Date: Aug. 31, 2006

(65) Prior Publication Data

US 2009/0124677 A1    May 14, 2009

Related U.S. Application Data

(60) Provisional application No. 60/685,912, filed on May 31, 2005.

(30) Foreign Application Priority Data

Feb. 28, 2005  (ES)  .................................. 200500485
Dec. 23, 2005  (ES)  .................................. 200503166

(51) Int. Cl.
    *C07D 257/00*  (2006.01)
(52) U.S. Cl. ..................................................... 548/250
(58) Field of Classification Search ................... 548/250
    See application file for complete search history.

(56) References Cited

U.S. PATENT DOCUMENTS 5,629,331  A   5/1997  Caron et al.
2002/0045650 A1  4/2002  Mackman

FOREIGN PATENT DOCUMENTS

| WO | WO 2004/039753 |   | 5/2004 |
|----|----------------|---|--------|
| WO | WO 2004/065383 | * | 8/2004 |
| WO | WO 2004/072064 |   | 8/2004 |
| WO | WO 2005/102987 |   | 11/2005 |

OTHER PUBLICATIONS

Form PCT/ISA/210 International Search Report dated May 30, 2006.
Larsen, R.D., et al., "Efficient Synthesis Of Losartan, A Nonpeptide Angiotensin II Receptor Antagonist"; Journal of Organic Chemistry, American Chemical Society, vol. 59, 1994, pp. 6391-6394.
Cousaert, N., et al. "Efficient, Protection-Free Suzuki-Miyaura Synthesis Of Ortho-Biphenyltetrazoles", Tetrahedron Letters, vol. 46, No. 38, Sep. 2005.
Murugesan, N., et al., "Biphenyslulfonamide Endothelin Receptor Antagonists. Part 3: Structure-Activity Relationship Of 4'-Heterocyclic Biphenylsulfonamides", Bioorganic And Medicinal Chemistry Letters, vol. 12, 2002, pp. 517-520.
Bernhart, C.A., et al., "A New Series Of Imidazolones: Highly Specific And Potent Nonpeptide AT1 Angiotensin II Receptor Antagonists", Journal of Medicinal Chemistry, American Chemical Society, vol. 36, No. 22, 1993, pp. 3371-3380.

* cited by examiner

*Primary Examiner*—Susannah Chung
(74) *Attorney, Agent, or Firm*—Cozen O'Connor

(57) ABSTRACT

It is provided a method for obtaining Irbesartan polymorph A, with few synthesis steps, by coupling the intermediate of formula (II) with the compound of formula (III), neutralising one of its alkaline salts in an aqueous medium and recrystallising the crude product obtained. The utilisation of said method obviates protection and deprotection of the tetrazole ring and is therefore of considerable interest for obtaining Irbesartan on a large industrial scale. The invention also refers to the synthesis intermediate of formula (II).

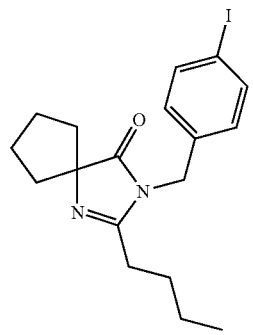

(II)

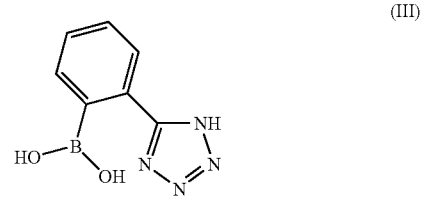

(III)

19 Claims, 1 Drawing Sheet

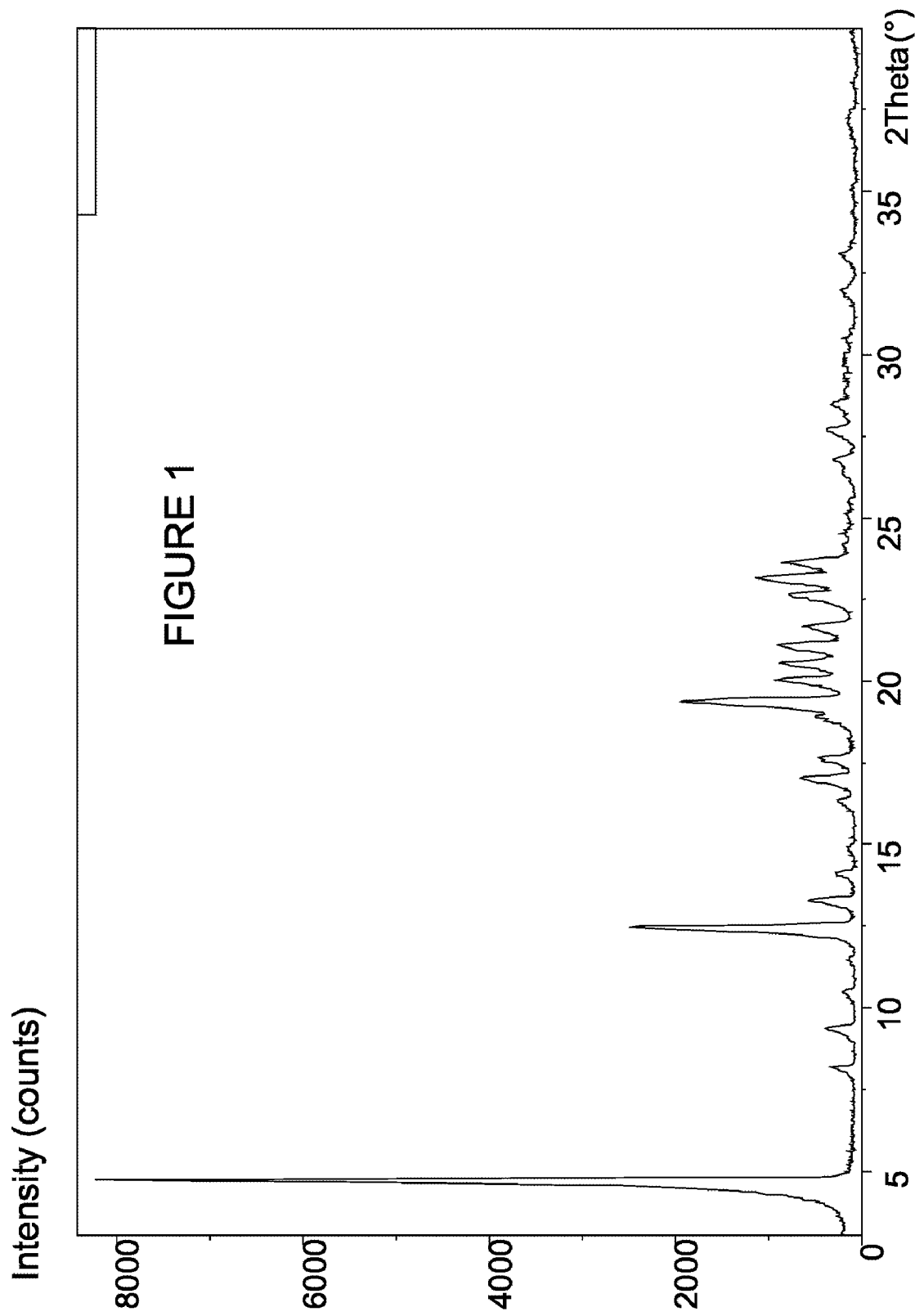

METHOD FOR OBTAINING A PHARMACEUTICALLY ACTIVE COMPOUND (IRBESARTAN) AND ITS SYNTHESIS INTERMEDIATE

FIELD OF THE INVENTION

The present invention relates to a method for obtaining a pharmaceutically active compound. It also relates to a synthesis intermediate useful for obtaining said pharmaceutically active compound and to the methods useful for obtaining said intermediate.

In particular, the present invention relates to a method for obtaining Irbesartan polymorph A, useful for manufacturing a medicament for treating arterial hypertension or heart failure.

BACKGROUND OF THE INVENTION

Irbesartan is a known angiotensin II receptor antagonist, the octapeptide produced by the action of the angiotensin converting enzyme and having considerable influence on blood pressure. The structure of Irbesartan is shown in (I).

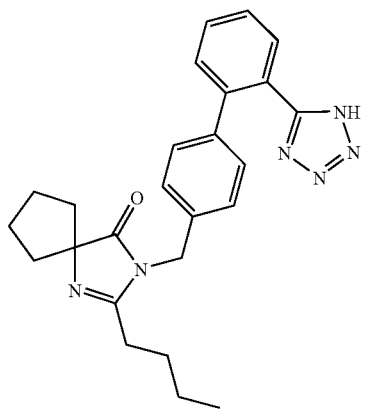

(I)

The synthesis of Irbesartan has been described in U.S. Pat. No. 5,270,317 and U.S. Pat. No. 5,559,233, among others. The antepenultimate reaction step consists in the reaction of a cyano group in the biphenyl ring with an azide, such as tributyltin azide. U.S. Pat. No. 5,270,317 discloses reaction times of up to 210 hours.

U.S. Pat. No. 5,629,331 also describes the synthesis of Irbesartan from the precursor 2-n-butyl-3-[(2'-cyanobiphenyl-4-yl)methyl]-1,3-diazaspiro-[4,4]non-1-en-4-one with sodium azide and triethylamine hydrochloride in an aprotic dipolar solvent, neutralisation of one of its alkaline salts in an aqueous medium and subsequent recrystallisation to obtain form A. The utilisation of azides involves safety risks, while aprotic dipolar solvents, such as N-methylpyrrolidone, have a relatively high boiling point and can be difficult to eliminate.

Patent WO 2004/065383 also describes the synthesis of Irbesartan tritylate by reacting 2-(1-trityl-1H-tetrazol-5-yl)phenylboronic acid with 2-butyl-3-(4'-bromobenzyl)-1,3-diazaspiro[4,4]non-1-en-4-one under Suzuki coupling conditions. The product so obtained is then submitted to acid conditions in order to hydrolyse the trityl group of the tetrazole ring in order to finally give Irbesartan. One negative aspect of said technique is the use of a voluminous protecting group such as trityl, which very considerably increases the molecular weight of the last synthesis intermediate, which last is then dramatically diminished in the final hydrolysis that provides Irbesartan, thereby resulting in a process of low atomic efficiency. This further creates a considerable amount of residual products and increases the number of synthesis steps in the process.

Patents DE4313747, DE4407488, U.S. Pat. No. 5,596,006, EP594022 and WO9609301 describe the synthesis of other biphenyl compounds by reacting an aryl halide with 2-(1H-tetrazol-5-yl)phenylboronic acid in the presence of a palladium catalyst.

A safe, ecological and high-yield method for obtaining Irbesartrán with few synthesis steps therefore remains necessary. Furthermore, it must be possible to apply said method on an industrial scale.

DESCRIPTION OF THE INVENTION

A first aspect of the present invention is to provide a method for obtaining Irbesartan polymorph A that allows it to be obtained rapidly and with high yields.

It is also a cleaner method from the environmental point of view, and safer in that it does not require the utilisation of azides or of aprotic dipolar solvents such as N-methylpyrrolidone, which have a relatively high boiling point and can be difficult to eliminate.

More advantageously still, the method defined according to the first aspect of the invention does not use protecting groups for the tetrazole ring of the compound of formula (III). This, together with the fact that the last synthesis step is a catalytic reaction, favours what is understood to be the atomic efficiency of the process, i.e. the proportion of atoms from the respective starting reagents that are incorporated into the desired product is optimal, and this shows itself in a considerable reduction of the amount of residues to be treated.

In accordance with the first aspect of the invention, a method is provided for obtaining Irbesartan polymorph A with few synthesis steps, by coupling the intermediate of formula (II) with the compound of formula (III), neutralising one of its alkaline salts in an aqueous medium and recrystallising the crude product obtained. The utilisation of said method obviates protection and deprotection of the tetrazole ring and is therefore of considerable interest for obtaining Irbesartan on a large industrial scale.

Said method also greatly simplifies the process of isolating and purifying the product. It obviates the extraction with toluene necessary to eliminate the N-methylpyrrolidone and other organic impurities from the aqueous solution of the alkaline salt of the product. The process uses a single organic solvent immiscible with water, such as ethyl acetate, thereby conferring an environmental improvement. An intermediate crystallisation of the crude product is also eliminated prior to final crystallisation in order to obtain the desired polymorph A.

A second aspect of the invention is the synthesis intermediate defined by formula (II).

A third aspect of the invention is to provide a method for obtaining the synthesis intermediate of formula (II).

A fourth aspect of the invention is to provide an alternative method for obtaining the synthesis intermediate of formula (II).

A fifth aspect of the invention is to provide yet another improved method for obtaining said synthesis intermediate of formula (II).

DEFINITIONS

The term "organic base" is taken to mean triethylamine, diisopropylamine (DIPEA), 1,4-diazabicyclo[2,2,2]octane (DABCO), morpholine and other ammonia derivatives in which one or more hydrogens have been substituted by alkyl or aryl radicals.

The term "inorganic base" is taken to mean a hydroxide or carbonate of a group I or group II metal, such as sodium carbonate, potassium carbonate, cesium carbonate, sodium hydroxide, potassium hydroxide, lithium hydroxide or potassium fluoride or potassium phosphate.

The term "biphasic system" is taken to mean a reaction medium that comprises two liquid phases, formed by a first and a second solvent that are immiscible with each other, or a system formed by a liquid phase and a solid phase. The first are organic solvents. Preferred though non-limiting examples are: 1,2-dimethoxyethane (DME), diethoxymethane (DEM), tetrahydrofuran (THF), hydrocarbons such heptane, cyclohexane, methylcyclohexane, toluene, xylenes, tetraline or decaline or mixtures thereof. The second solvent can be water, preferably containing the inorganic base. Another biphasic system consists in at least one solvent selected from between the first and second solvents mentioned above, and the utilisation of one of the inorganic bases in solid form.

The term "palladium catalyst" is taken to mean a compound of palladium, which can be homogeneous and soluble in the reaction medium, such as $Pd(PPh_3)_4$, $PdCl_2(PPh_3)_4$, $Pd(AcO)_2$, or heterogeneous and insoluble in the reaction medium, such as Pd/C.

The term "ligand" is taken to mean an organic compound of the phosphine or amine type capable of coordinating and activating the palladium species that catalyses the desired reaction, such as triphenylphosphine, diphenylphosphine ethylene (DPPE), bis-diphenylphosphine ferrocene (DPPF), tri-(t-butyl)phosphine, tri-(o-tolyl)phosphine, tricyclohexylphosphine, trisodium salt of 3,3',3"-phosphinidinatris (benzene-sulphonate) (TPPTS).

DESCRIPTION OF THE FIGURES

FIG. 1 shows an X ray diffractogram of compound (I) form A obtained according to Example 9.

DETAILED DESCRIPTION OF THE INVENTION

The present invention has the object of providing a new method for obtaining Irbesartan of formula (I),

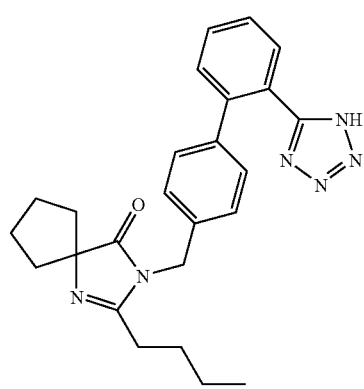

(I)

that permits it to be obtained with good yields and that presents no problematic safety or environmental aspects.

The method for obtaining Irbesartan, or a pharmaceutically acceptable salt thereof, in accordance with the first aspect of the invention, is characterized in that it comprises:

(a) a coupling reaction of the compound of formula (II) with the 2-(1H-tetrazol-5-yl)phenylboronic acid of formula (III):

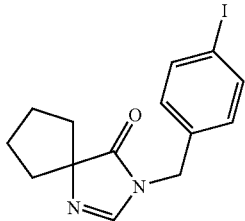

(II)

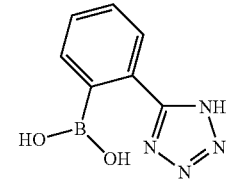

(III)

in a solvent medium selected from polar organic or aqueous, or a mixture of water and water-miscible solvent or a biphasic system, in the presence of an organic or inorganic base, capable of forming a salt with the tetrazole ring of the compound of formula (III), at a temperature between 25 and 150° C., with a palladium catalyst and, if required, a ligand, to obtain the Irbesartan of formula (I) in the form of an aqueous solution of one of its organic- or inorganic-base salts;

(b) the above aqueous alkaline solution is acidified to pH 4.8 to 5.2 and the precipitate so obtained is filtered; and (c) the product of stage (b) is recrystallised in the presence of an organic solvent or a mixture thereof with water, preferably in a proportion between 1% and 20% by volume, to give Irbesartan polymorph A with the following X-ray diffraction spectrum:

| Pos.[°2Th.] | d-spac. [Å] | Rel. Int.[%] |
| --- | --- | --- |
| 4.76 | 18.561 | 100 |
| 8.20 | 10.783 | 2.71 |
| 9.43 | 9.377 | 2.8 |
| 10.54 | 8.396 | 1.72 |
| 12.50 | 7.080 | 35.21 |
| 13.32 | 6.646 | 4.4 |
| 14.13 | 6.268 | 1.8 |
| 16.37 | 5.415 | 1.61 |
| 17.03 | 5.207 | 8.25 |
| 17.67 | 5.021 | 3.06 |
| 18.90 | 4.696 | 3.76 |
| 19.44 | 4.567 | 13.86 |
| 20.06 | 4.426 | 8.16 |
| 20.59 | 4.314 | 6.94 |
| 21.13 | 4.204 | 7.03 |
| 21.69 | 4.097 | 6.4 |
| 22.67 | 3.923 | 5.66 |
| 23.19 | 3.835 | 11.07 |
| 23.68 | 3.758 | 7.84 |
| 26.42 | 3.374 | 1.27 |
| 26.83 | 3.324 | 2.05 |

-continued

| Pos.[°2Th.] | d-spac. [Å] | Rel. Int.[%] |
|---|---|---|
| 27.70 | 3.220 | 3.22 |
| 28.52 | 3.130 | 2.57 |
| 31.96 | 2.800 | 1.52 |
| 33.06 | 2.710 | 1.82 |

Advantageously, this coupling takes place without need for the use of protecting groups for the tetrazole ring of the compound of formula (III). The reaction is effected in the presence of an organic or inorganic base capable of forming a salt with the tetrazole ring and in the presence of catalytic amounts of a palladium compound. The reaction can be carried out in an organic polar or aqueous solvent, or a mixture of water and a water-miscible solvent, or in a biphasic system at a temperature between 25° C. and 150° C., preferably between 50° C. and 120° C., more preferably still between 70° C. and 90° C.

Preferably, in stage (a) the solvent medium is selected from among the solvents THF, DME, DEM, toluene, xylene, methanol, ethanol, propanol, decaline and water, or mixtures thereof, and said organic base is selected from TEA, DIPEA, DABCO, morpholine and other ammonia derivatives in which one or more hydrogens have been substituted by alkyl or aryl radicals such as ethyl, isopropyl, benzyl or phenyl, and said inorganic base is selected from sodium carbonate, potassium carbonate, cesium carbonate, sodium hydroxide, potassium hydroxide, potassium fluoride or potassium phosphate.

This coupling can be carried out in homogeneous phase, if the palladium compound is soluble in the reaction medium, such as $Pd(PPh_3)_4$, $PdCl_2(PPh_3)_4$, $Pd(AcO)_2$, or in heterogeneous phase if the palladium compound is insoluble in the reaction medium, as is the case of Pd/C. If Pd/C is used, the coupling reaction requires the presence of catalytic amounts of a ligand, preferably of phosphine type, especially triphenylphosphine or a phosphine soluble en water, such as the trisodium salt of 3,3',3"-phosphinidinatris(benzene-sulphonate) or the sodium salt of diphenylphosphinebenzene-3-sulphonic acid. These last present the advantage of it being possible to carry out the reaction using water as solvent.

Preferably, in stage (c) the organic solvent is selected from at least one alcohol such as methanol, ethanol, propanol or isopropanol, one ester such as ethyl acetate or isopropyl acetate, one ether such as tetrahydrofuran, dioxane, dimethoxyethane or diisopropyl ether, a ketone such as butanone, methyl isopropylketone or methyl isobutylketone or a hydrocarbon such as heptane, toluene, xylene.

Preferably, the solvent selected in stage (c) is isopropanol, because it lends the product higher purity and better recovery.

A second aspect of the invention is to provide a synthesis intermediate of formula (II):

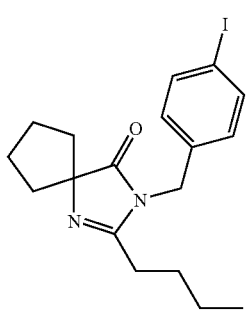

(II)

Utilisation of the synthesis intermediate of formula (II) in obtaining Irbesartan permits it to be obtained with surprisingly high yields, with cleaner reaction crude products and furthermore avoiding decomposition of the compound of formula (III), which means that the reaction with the synthesis intermediate of formula (II) continues until the starting product have been used up.

The synthesis intermediate 2-butyl-3-(4'-iodobenzyl)-1,3-diazaspiro[4,4]non-1-en-4-one of formula (II) can be prepared by reaction, under phase-transfer conditions, between the 2-butyl-1,3-diazaspiro[4,4]non-1-en-4-one hydrochloride of formula (IV) and the 4-iodobenzyl bromide.

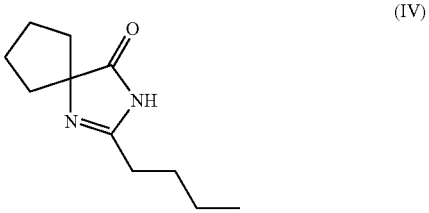

(IV)

The compound 2-butyl-1,3-diazaspiro[4,4]non-1-en-4-one of formula (IV) is a commercially available compound. Said reaction takes place in a biphasic system, in the presence of an inorganic base, and in the presence of a phase-transfer catalyst, with vigorous stirring for 1 hour at a temperature between 50° C. and 120° C. Once the reaction has finished, the system is left to cool, the phases are separated and the organic phase is evaporated to give a crude product. That crude product is dissolved in a suitable solvent such as ethyl acetate or isopropyl acetate, and the equivalent amount of concentrated hydrochloric acid is added to it to give after filtering the compound of formula (II) as a hydrochloride of high purity and with excellent yield.

The compound 2-butyl-3-(4'-iodobenzyl)-1,3-diazaspiro [4,4]non-1-en-4-one of formula (II) can also be obtained by amidation of a 1-amino-cyclopentanocarboxylic acid protected as tert-butoxycarbonylamine, as benzyloxycarbonylamine or as pentanoylamine, with the 4-iodobenzylamine, in the presence of an organic solvent and a condensing agent, to provide a diamide, which after:

a) cyclising in a reaction catalysed with acid or thermally, provides the compound of formula (II) in accordance with Scheme 1; or b) deprotecting the protecting group under acid conditions or in the presence of hydrogen and a platinum catalyst to provide the 4-iodobenzylamide of the 1-amino-1-cyclopentanocarbo-xylic acid of formula (IX)

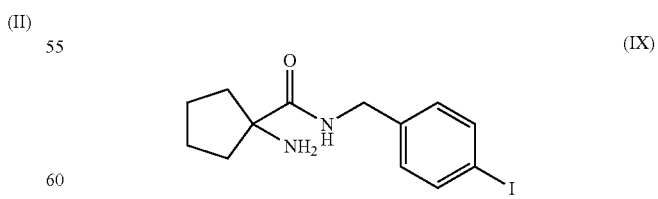

(IX)

which, followed by reaction with trimethyl orthovalerate in the presence of a catalytic amount (1-5%) of a carboxylic acid such as acetic or formic sulphonic acid such as methanesulphonic or toluenesulphonic acid provides the synthesis intermediate of formula (II), in accordance with Scheme 2.

On the one hand, the compound 2-butyl-3-(4'-iodobenzyl)-1,3-diazaspiro[4,4]non-1-en-4-one of formula (II) can be obtained according to Scheme 1 below:

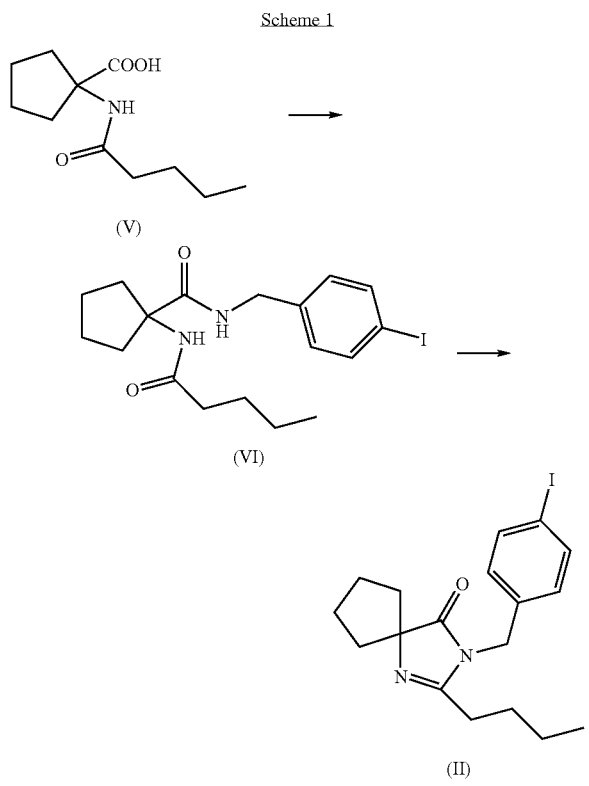

In which amidation of the 1-pentanoylamine-cyclopentanocarboxylic acid (V) (compound described in G. Winters et al., Il Farmaco, Ed. Sc. 1966, 21, 624) with 4-iodobenzylamine in an apolar solvent and in the presence of a condensing agent provides the diamide of formula (VI). Solvents suitable for this reaction are dichloromethane, acetonitryl, THF, ethyl acetate, dimethylformamide (DMF), dimethyl acetamide (DMA), N-methylpyrrolydinone (NMP), especially DMF. Condensing agents are agents that facilitate the reaction between a carboxylic acid and an amine to form amides. Amongst the ones used are dicyclohexyl carbodiimide (DCC), dimethylaminopropyl carbodiimide (WSC), carbonyl diimidazole (CDI), diphenylphosphoryl azide (DPPA), diethylphosphoryl cyanide (DEPC), benzotriazolyloxy-tris (dimethylaminophosphonium hexafluorophosphate (BOP), especially BOP. This compound of formula (VI) can be cyclised in a reaction catalysed with acid or thermally to give the compound of formula (II).

Further, the compound 2-butyl-3-(4'-iodobenzyl)-1,3-diazaspiro[4,4]non-1-en-4-one of formula (II) can be obtained according to Scheme 2 below.

Amidation of the 1-tert-butoxycarbonylamine-cyclopentanocarboxylic (VII) acid (compound described in E. P. Johnson et al., Org. Proc. Res. & Dev. 1998, 2, 238) with 4-iodobenzylamine under the conditions described above provides the diamide (VIII). Deprotection of the protecting group BOC under acid conditions provides the 4-iodobenzylamide of the 1-amino-1-cyclopentanocarboxylic acid of formula (IX). This compound of formula (IX) reacts with trimethyl orthovalerate in the presence of catalytic amounts of acid to give the compound of formula (II).

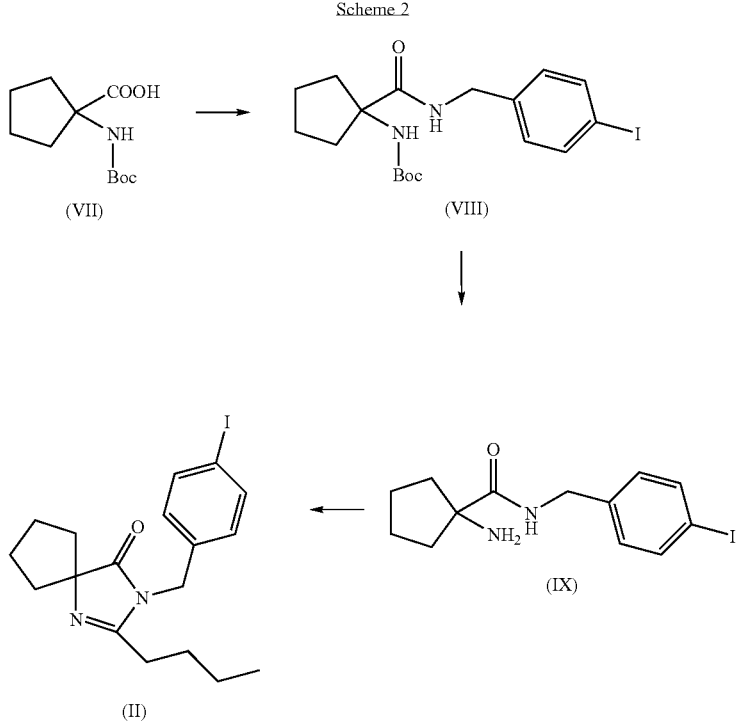

The present invention further provides an alternative method for obtaining the synthesis intermediate of formula (II) that does not require 4-iodobenzylamine, an extremely expensive reagent that is difficult to obtain.

The present inventors have found that it is possible to prepare the synthesis intermediate of formula (II) by using the compound 4-iodobenzylbromide, a reagent obtainable industrially at a reasonable price.

Said alternative method includes (see Scheme 3 below) obtaining the synthesis intermediate of formula (II):

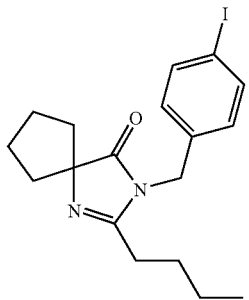
(II)

by the reaction of the 1-pentanoylamine-cyclopentanocarboxamide of formula (X) with 4-iodobenzyl bromide,

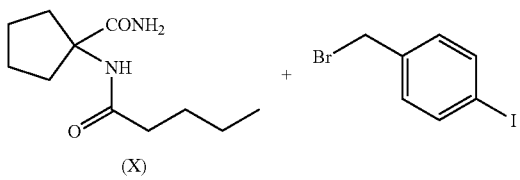
(X)

in the presence of a phase-transfer catalyst in a biphasic reaction system.

Advantageously, one of said phases includes 1,2-dimethoxyethane (DME), diethoxymethane (DEM), tetrahydrofuran (THF) or an aliphatic or aromatic hydrocarbon, and said other phase is water that can contain an inorganic base, or said other phase can be an inorganic base in solid form.

Also advantageously, prior to reaction with 4-iodobenzyl bromide, the 1-pentanoylamine-cyclopentanocarboxamide of formula (X) is in an aqueous suspension that can include an inorganic base.

Preferably, said inorganic base is selected from KOH, NaOH, LiOH, $Na_2CO_3$ and $K_2CO_3$. More preferably still, said inorganic base is KOH.

Advantageously, prior to reaction with the 1-pentanoylamine-cyclopentanocarboxamide of formula (X), the 4-iodobenzyl bromide is in a solution including 1,2-dimethoxyethane (DME), diethoxymethane (DEM), tetrahydrofuran (THF) or an aliphatic hydrocarbon such as heptane, cyclohexane, methylcyclohexane, or an aromatic hydrocarbon such as toluene, xylene, decaline or tetraline. Preferably, said aromatic hydrocarbon is toluene.

The reaction between the 1-pentanoylamine-cyclopentanocarboxamide of formula (X) and 4-iodobenzyl bromide is carried out in the presence of a phase-transfer catalyst such as salts of ammonium or of quaternary phosphonium, polyethylene glycol derivatives, crown ethers or cryptands, which will preferably be acid sulphate of tetrabutylammonium.

Scheme 3 in accordance with the present invention is included below:

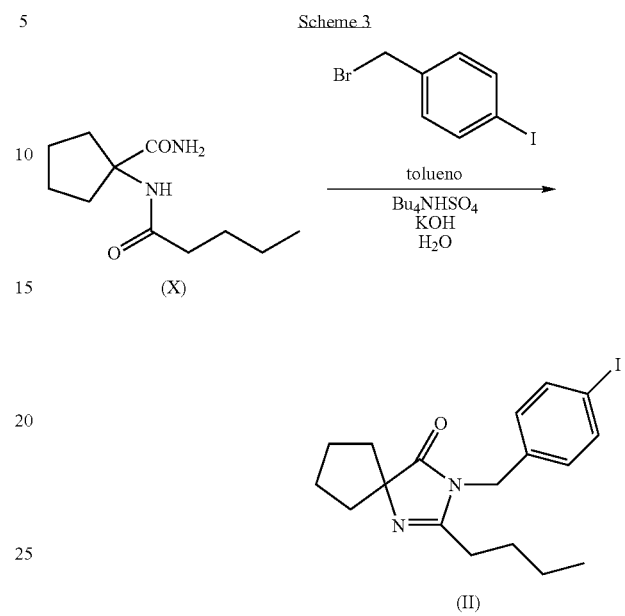

Advantageously, in accordance with the invention Irbesartan is obtained with good chemical yield and high optical purity, by means of methods applicable at industrial scale, cleaner from the environmental viewpoint and also safer.

There follow some examples that by way of non-restrictive illustration of the invention show preferred embodiments of the various aspects thereof.

EXAMPLES

Example 1

Obtaining 2-butyl-3-(4'-iodobenzyl)-1,3-diazaspiro[4,4]non-1-en-4-one (II)

A solution of 23.07 g (100 mmol) of the hydrochloride of 2-butyl-1,3-diazaspiro[4,4]non-1-en-4-one and 19.8 g of potassium hydroxide in 100 mL de water is added to a solution of 29.7 g (100 mmol) of 4-iodobenzyl bromide and 3.4 g (10 mmol) of tetrabutylammonium bisulphate in 30 mL of toluene, and the mixture is heated at reflux for 1 hr. After cooling to 25° C., 100 mL of water is added and the phases are separated. To the organic phase is added 10 mL of concentrated hydrochloric acid, 100 mL is evaporated at reduced pressure, 300 mL of ethyl acetate is added and the resulting solid is filtered to give 39.6 g (88%) of the title compound in the form of hydrochloride.

DSC (min.): 82° C.

IR (KBr, cm-1): 3500, 3420, 2940, 1770, 1630, 1500.

RMN 1H (CDCl3), δ (ppm): 0.80 (t, 3H, CH3), 1.30-1.50 (m, 2H, —CH2-CH3), 1.55-1.80 (m, 2H, —CH2-CH2-CH$_3$), 1.80-2.40 (m, 8H, cyclopentane), 2.95 (t, 2H, CH2-C—N), 4.85 (s, 2H, CH2-Ar), 6.95 (d, 2H, H—Ar), 7.75 (d, 2H, H—Ar).

Example 2

Obtaining the 4-iodobenzylamide of 1-pentanoylamine-cyclopentanocarboxylic acid (VI)

8.2 g (18.6 mmol) of BOP is added to a suspension of 3.96 g (18.6 mmol) of 1-pentanoylamine-cyclopentanocarboxylic acid, 5.0 g (18.6 mmol) of hydrochloride of 4-iodobenzylamine and 6.5 mL (37.2 mmol) of diisopropylamine in 40 mL of dimethylformamide, and this is stirred for 10 hr. The reaction mixture is poured onto a mixture of EtOAc (400 mL) and water (400 mL) and stirred for 30 min. Following decanting, the organic phase is washed with saturated solution of sodium bicarbonate (200 mL×2), with 5% solution of sodium bisulphite (200 mL), with saturated solution of sodium chloride (100 mL), dried with magnesium sulphate and evaporated. The residue is recrystallised from 60 mL of toluene to give 6.0 g (75%) of the title compound in the form of a white solid.

M.p.=150-152° C.
IR (KBr, cm-1): 3340, 3280, 1660, 1650, 1540.
RMN 1H (DMSO-d6), δ (ppm): 0.80 (t, 3H, CH3), 1.10-2.20 (m, 14H), 4.20 (d, 2H, CH2-Ar), 7.05 (d, 2H, H—Ar), 7.60 (d, 2H. H.Ar).

Example 3

Obtaining 2-butyl-3-(4'-iodobenzyl)-1,3-diazaspiro[4,4]non-1-en-4-one (II) (according to Scheme 1)

1.0 g (2.33 mmol) of the compound of Example 2 is heated to 250° C. under a current of nitrogen for 2 hr. The product thus obtained is purified by silica gel column chromatography, eluting with a 1:1 mixture of heptane/ethyl acetate, to obtain 400 mg (42%) of the title compound in the form of a colourless oil.

IR (film, cm-1): 2960, 2860, 1700, 1620, 1460, 1320.
RMN 1H (CDCl$_3$), δ (ppm): 0.90 (t, 3H, CH3), 1.10-2.10 (m, 14H), 2.30 (t, 2H, CH2-C—N), 4.60 (s, 2H, CH2-Ar), 6.90 (d, 2H, H—Ar), 7.65 (d, 2H, H—Ar).

Example 4

Obtaining 4-iodobenzylamide of 1-tert-butoxycarbonylamine-cyclopentanocarboxylic acid (VIII)

Following the method described in Example 2, and starting with 1.26 g (5.5 mmol) of 1-tert-butoxycarbonylamine-cyclopentanocarboxylic acid, 1.80 g (74%) of the title compound is obtained in the form of a white solid.

M.p.=185-187° C.
IR (KBr, cm-1): 3340, 2980, 1690, 1650, 1520.
RMN 1H (DMSO-d6), δ (ppm): 1.10-2.10 (m, 17H), 4.20 (d, 2H), 6.90-7.10 (m, 3H), 7.60 (d, 2H), 8.10 (sa, H—N).

Example 5

Obtaining the 4-iodobenzylamide of 1-amino-cyclopentanocarboxylic acid (IX)

5 mL of trifluoroacetic acid is added to a solution of 1.40 g (3.15 mmol) of the compound of Example 4 in 10 mL of dichloromethane. After 15 min. this is poured onto a mixture of ethyl acetate (200 mL), saturated solution of sodium bicarbonate (200 mL) and 20% sodium hydroxide (2.0 mL). The phases are separated and the organic phase is washed with saturated solution of sodium chloride, dried with magnesium sulphate and evaporated to give 1.0 g (92%) of the title compound in the form of a white solid.

M.p.=67-69° C.
IR (KBr, cm-1): 3400, 2980, 1650, 1510, 1490.
RMN 1H (DMSO-d6), δ (ppm): 1.30-2.20 (m, 8H, cyclopentane), 4.22 (d, 2H, CH2-Ar), 7.02 (d, 2H, H—Ar), 7.65 (d, 2H, H—Ar), 8.55 (sa, H—N).

Example 6

Obtaining 2-butyl-3-(4'-iodobenzyl)-1,3-diazaspiro[4,4]non-1-en-4-one (II) (according to Scheme 2)

A solution of 850 mg (2.47 mmol) of the compound of Example 5, 1.0 mL (5.80 mmol) of trimethyl orthovalerate and 0.1 mL (1.75 mmol) of acetic acid in 5 mL of dichloromethane is heated to 90° C. for 45 min. After evaporating, the residue is purified by silica gel column chromatography, eluting with heptane/ethyl acetate 2:1. By evaporating the correct fractions, 400 mg (39%) of the title compound is obtained in the form of a colourless oil, with the same spectroscopic data as described in Example 3.

Example 7

Obtaining 2-butyl-3-[2'-(1H-tetrazol-5-yl)-biphenyl-4-ilmethyl]-1,3-diazaspiro[4,4]non-1-en-4-one (I) (Irbesartan)

A solution of 2.0 g (4.9 mmol) de 2-butyl-3-(4'-iodobenzyl)-1,3-diazaspiro[4.4]non-1-en-4-one (II), 1.10 g (4.9 mmol) of 2-(1H-tetrazol-5-yl)phenylboronic acid (III), 780 mg (19.6 mmol) of sodium hydroxide and 283 mg (0.245 mmol) of palladium tetraquistriphenylphosphine in 20 mL of methanol is purged with gentle bubbling of nitrogen for 5 min and is heated at reflux for 1 hr.

After cooling to 20° C., it is diluted with ethyl acetate (100 mL) and water (50 mL), and 5.0 g of citric acid is added. The phases are separated, the organic phase evaporated and the residue purified by silica gel chromatography (eluent dichloromethane/methanol/ammonia at 500:50:5), to obtain 1.83 g (86%) of the compound (I) in the form of a white solid.

RMN 1H (CDCl3), δ (ppm): 0.80 (t, 3H, CH3), 1.10-1.35 (m, 2H, CH2-CH3), 1.35-1.60 (m, 2H, CH2-CH2-CH3), 1.60-1.95 (m, 8H, cyclopentyl), 2.15 (t, 2H, CH2-C—N), 4.60 (s, 2H, CH2-Ar), 7.05 (d, 2H, H—Ar), 7.15 (d, 2H, H—Ar), 7.45 (d, 1H, H—Ar), 7.50-7.70 (m, 2H, H—Ar), 7.90 (d, 2H, H—Ar ortho to the tetrazole).

Example 8

Obtaining 2-butyl-3-[2'-(1H-tetrazol-5-yl)-biphenyl-4-ilmethyl]-1,3-diazaspiro[4,4]non-1-en-4-one (I) (Irbesartan)

A solution of 2.051 g (5.0 mmol) de 2-butyl-3-(4'-iodobenzyl)-1,3-diazaspiro[4.4]non-1-en-4-one (II), 1.13 g (5.0 mmol) of 2-(1H-tetrazol-5-yl)phenylboronic acid (III), 800 mg (20.0 mmol) of sodium hydroxide, 262 mg (1.0 mmol) of triphenylphosphine and 44 mg (0.25 mmol) of palladium chloride in 20 mL of methanol is purged with gentle bubbling of nitrogen for 5 min and is heated at reflux for 1 hr. After cooling to 20° C., it is diluted with ethyl acetate (100 mL) and water (50 mL), and 5.0 g of citric acid is added. The phases are separated, the organic phase evaporated and the residue purified by silica gel chromatography (eluent dichloromethane/ methanol/ammonia at 500:50:5), to obtain 1.77 g (83%) of the compound (I) in the form of a white solid.

Example 9

Obtaining 2-butyl-3-[2'-(1H-tetrazol-5-yl)-biphenyl-4-ilmethyl]-1,3-diazaspiro[4,4]non-1-en-4-one (I) (Irbesartan)

A suspension of 2.0 g (4.9 mmol) of 2-butyl-3-(4'-iodobencyl)-1,3-diazaspiro[4,4]non-1-en-4-one(II), 1.10 g (4.9 mmol) of 2-(1H-tetrazol-5-yl)phenylboronic acid (III), 780 mg (19.6 mmol) of sodium hydroxide, 56.5 mg (0,216 mmol) of triphenylphosphine and 420 mg of 5% Pd/C in paste form (0.098 mmol of palladium) in 20 mL of methanol is heated at reflux for 3 h. After cooling to 20° C., it is diluted with ethyl acetate (50 mL) and water (150 mL), the catalyst is filtered, the phases are separated and to the aqueous phase is added 3N hydrochloric acid to pH 5.0. This is filtered and the solid obtained is recrystallised from 2-propanol, to obtain 1.45 g (69%) of the compound (I) form A (FIG. 1) as a white solid.

Example 10

Obtaining 2-butyl-3-(4'-iodobenzyl)-1,3-diazaspiro[4,4]non-1-en-4-one (II) (according to Schema 3)

A solution of 2.97 g (10.0 mmol) of 4-iodobenzyl bromide in 30 mL of toluene is added dropwise to a stirred suspension of 2.12 g (10.0 mmol) of 1-pentanoylamine-cyclopentanocarboxamide (X), 1.78 g (27.0 mmol) of KOH and 0.51 g (1.5 mmol) of TBAHS in 10 mL of water. It is stirred for 30 min. at 25° C. and then heated at 70° C. for 3 hr. After cooling to 25° C., 30 mL of water is added and the phases are separated. The aqueous phase is extracted with 30 mL of toluene and the combined organic phases are washed with saturated solution of NaCl (30 mL) and evaporated.

The residue is purified by silica gel column chromatography, eluting with a mixture of heptane/ethyl acetate 1:1, to obtain 2.87 g (70%) of the title compound in the form of a colourless oil, with the same spectroscopic data as described in Example 1 above.

Advantageously, in accordance with the method of Scheme 3 better yields of the synthesis intermediate of formula (II) are obtained.

The invention claimed is:
1. Method for obtaining a pharmaceutically active compound, Irbesartan polymorph A, or a pharmaceutically acceptable salt thereof, which comprises:
  (a) a coupling reaction of the compound of formula (II) with the 2-(1H-tetrazol-5-yl)phenylboronic acid of formula (III):

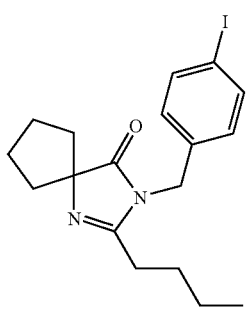
(II)

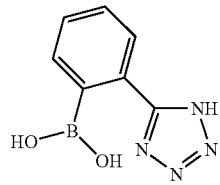
(III)

in a solvent medium selected from an organic polar or aqueous solvent, or a mixture of water and water-miscible solvent or a biphasic system, in the presence of an organic or inorganic base, capable of forming a salt with the tetrazole ring of the compound of formula (III), at a temperature between 25 and 150° C., with a palladium catalyst and, if required, a phosphine ligand, to obtain Irbesartan (1):

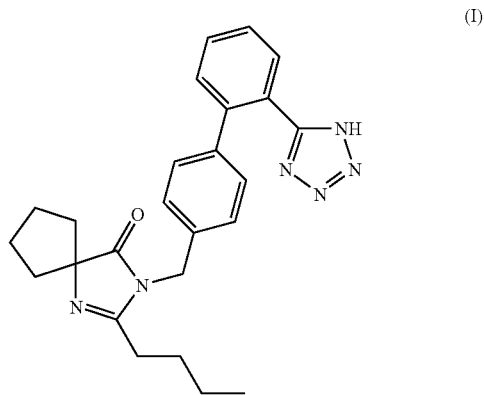
(I)

in the form of an aqueous solution of one its organic- or inorganic-base salts;
  (b) the preceding aqueous alkaline solution is acidified to pH 4.8 to 5.2 and the precipitate so obtained is filtered; and
  (c) the product of stage (b) is recrystallised in the presence of an organic solvent or a mixture thereof with water to give Irbesartan polymorph A with the following X-ray diffraction spectrum:

| Pos.[°2Th.] | d-spacing [Å] | Rel. Int.[%] |
| --- | --- | --- |
| 4.76 | 18.561 | 100 |
| 8.20 | 10.783 | 2.71 |
| 9.43 | 9.377 | 2.8 |
| 10.54 | 8.396 | 1.72 |
| 12.50 | 7.080 | 35.21 |
| 13.32 | 6.646 | 4.4 |
| 14.13 | 6.268 | 1.8 |
| 16.37 | 5.415 | 1.61 |
| 17.03 | 5.207 | 8.25 |
| 17.67 | 5.021 | 3.06 |
| 18.90 | 4.696 | 3.76 |
| 19.44 | 4.567 | 13.86 |
| 20.06 | 4.426 | 8.16 |
| 20.59 | 4.314 | 6.94 |
| 21.13 | 4.204 | 7.03 |
| 21.69 | 4.097 | 6.4 |
| 22.67 | 3.923 | 5.66 |
| 23.19 | 3.835 | 11.07 |
| 23.68 | 3.758 | 7.84 |

-continued

| Pos.[°2Th.] | d-spacing [Å] | Rel. Int.[%] |
|---|---|---|
| 26.42 | 3.374 | 1.27 |
| 26.83 | 3.324 | 2.05 |
| 27.70 | 3.220 | 3.22 |
| 28.52 | 3.130 | 2.57 |
| 31.96 | 2.800 | 1.52 |
| 33.06 | 2.710 | 1.82. |

2. Method according to claim 1, wherein in stage (a) the coupling reaction is carried out at a temperature between 50° C. and 120° C.

3. Method according to claim 2, in which the temperature is between 70° C. and 90° C.

4. Method according to claim 1, wherein in stage (a) the solvent medium is selected from the solvents THF, DME, DEM, toluene, xylene, methanol, ethanol, propanol, decaline and water, or mixtures thereof.

5. Method according to claim 1, wherein in stage (a) said organic base is selected from TEA, DIPEA, DABCO, morpholine and other ammonia derivatives in which one or more hydrogens have been substituted by alkyl or aryl radicals.

6. Method according to claim 5, in which said alkyl or aryl radicals are selected from ethyl, isopropyl, benzyl or phenyl.

7. Method according to claim 1, wherein in stage (a) said inorganic base is selected from sodium carbonate, potassium carbonate, cesium carbonate, sodium hydroxide, potassium hydroxide, potassium fluoride or potassium phosphate.

8. Method according to claim 1, wherein in stage (a) said coupling is carried out in homogeneous phase, if the palladium compound is soluble in the reaction medium, or in heterogeneous phase if the palladium compound is insoluble in the reaction medium.

9. Method according to claim 8, wherein if the palladium compound is soluble in the reaction medium it is selected from $Pd(PPh_3)_4$, $PdCl_2(PPh_3)_4$, $Pd(AcO)_2$ or $PdCl_2$.

10. Method according to claim 8, wherein if the palladium compound is insoluble in the reaction medium it is selected from Pd/C or another type of palladium compound supported or anchored within a polymer and the coupling reaction is carried out in the presence of catalytic amounts of a phosphine ligand.

11. Method according to claim 10, wherein said phosphine ligand is triphenylphosphine or a phosphine soluble in water.

12. Method according to claim 11, wherein said phosphine soluble in water is the trisodium salt of 3,3',3''-phosphinidinatris(benzenesulphonate).

13. Method according to claim 1, wherein in stage (c) the organic solvent is selected from at least an alcohol, an ester, an ether, a ketone or a hydrocarbon.

14. Method according to claim 13, in which said alcohol is selected from methanol, ethanol, propanol or isopropanol.

15. Method according to claim 13, in which said ester is selected from ethyl acetate or isopropyl acetate.

16. Method according to claim 13, in which said ether is selected from tetrahydrofuran, dioxane, dimethoxyethane or diisopropyl ether.

17. Method according to claim 13, in which said ketone is selected from butanone, methyl isopropylketone or methyl isobutylketone.

18. Method according to claim 13, in which said hydrocarbon is selected from heptane, toluene, xylene.

19. Method according to claim 1, wherein in stage (c) the product from stage (b) is recrystallised in the presence of a mixture of an organic solvent or a mixture thereof with water preferably with a proportion of water between 1% and 20% by volume.

* * * * *